United States Patent [19]

Ducloux

[11] Patent Number: 4,620,090

[45] Date of Patent: Oct. 28, 1986

[54] METHOD AND APPARATUS FOR OPTICAL INSPECTION OF TRANSPARENT ARTICLES

[75] Inventor: Marcel L. Ducloux, Carrieres sur Seine, France

[73] Assignee: Saint-Gobain Cinematique et Controle, Gennevilliers, France

[21] Appl. No.: 691,595

[22] Filed: Jan. 15, 1985

[30] Foreign Application Priority Data

Jan. 17, 1984 [FR] France ............................... 84 00657

[51] Int. Cl.$^4$ ...................... G01N 21/90; G01N 21/15
[52] U.S. Cl. .................................. 250/223 B; 250/224; 356/240
[58] Field of Search ............................ 250/223 B, 224; 356/240, 400

[56] References Cited

U.S. PATENT DOCUMENTS

| | | | |
|---|---|---|---|
| 3,338,130 | 8/1967 | Gaffard | 356/431 |
| 3,361,025 | 1/1968 | Gaffard | 356/239 |
| 3,410,643 | 11/1968 | Jorgensen | 356/200 |
| 3,851,975 | 12/1974 | Serret | 356/198 |
| 3,942,001 | 3/1976 | O'Connor | 250/223 |
| 3,987,301 | 10/1976 | O'Connor | 250/227 |
| 3,989,387 | 11/1976 | Hategan | 356/239 |
| 4,293,219 | 10/1981 | Ducloux | 356/240 |
| 4,368,982 | 1/1983 | Van Arnam et al. | 250/224 X |

FOREIGN PATENT DOCUMENTS 2001751 2/1979 United Kingdom .

*Primary Examiner*—Eugene R. LaRoche
*Assistant Examiner*—D. C. Mis
*Attorney, Agent, or Firm*—Pennie & Edmonds

[57] ABSTRACT

A method and an apparatus for optical inspection of transparent articles. The method and apparatus use a light beam scanning field which is separated into at least two portions. The field portions are directed at the article at differing angles of incidence such that they eliminate blind spots caused by portions of the apparatus which block the passage of the light through the article. A feature of the invention is its provision of a folded optical path to increase the length the beam travels between the beam generator and the object beyond the physical distance between the beam generator and the object.

20 Claims, 6 Drawing Figures

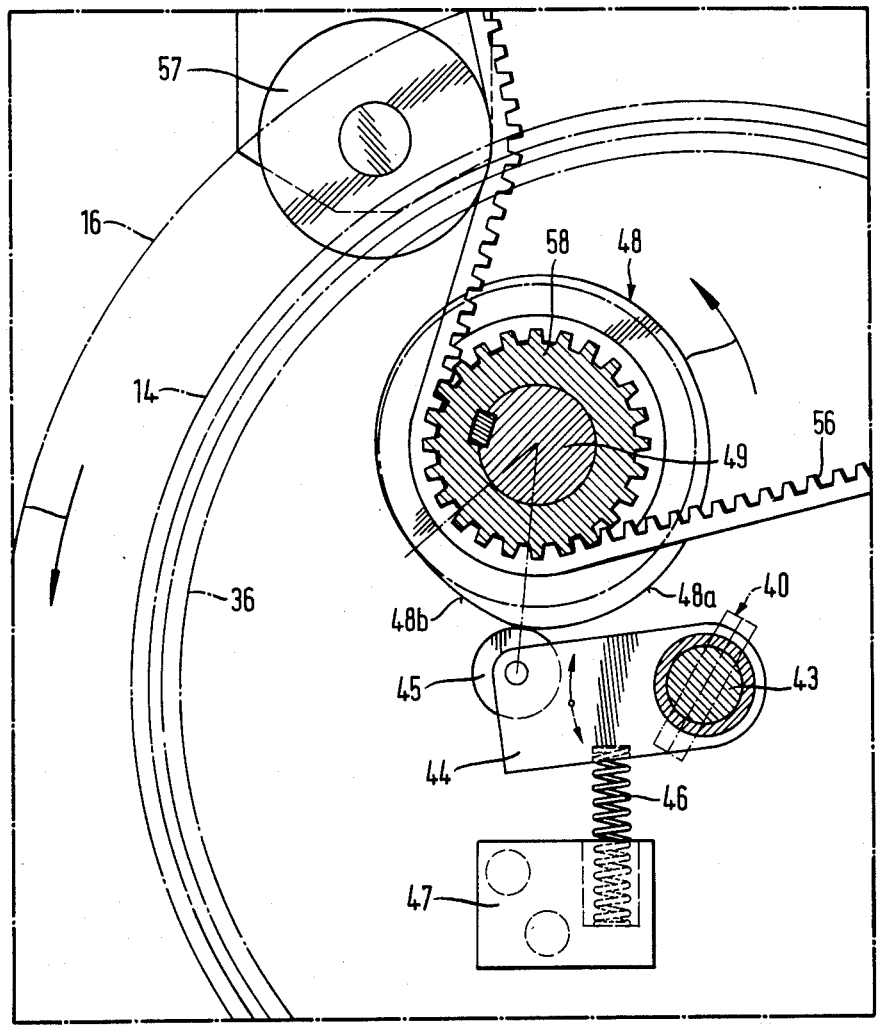

METHOD AND APPARATUS FOR OPTICAL INSPECTION OF TRANSPARENT ARTICLES

BACKGROUND OF THE INVENTION

1. Field of the Invention

The invention relates to the automated inspection of articles and in particular to optical inspection of transparent or translucent articles at high speeds.

2. Background Information

Production and use of transparent or translucent articles made of plastic or glass such as bottles, jars and vials invariably require optical inspection. This inspection must take place at the high speeds found on production lines.

In order to perform the inspection properly, it must be performed on the most sensitive zones of the article around its entire perimeter. This is normally achieved by inspecting the article while turning it at least one full turn. A known method of performing an overall check of the article at high speeds comprises reading a photosensitive screen illuminated by a light beam which scans the article in successive diametral planes during rotation of the article.

It is advantageous to use a laser beam to scan the article because the intensity and collimation of the laser beam eliminate the need for focusing elements used with other scanning beams. Advantageously, the laser beam should be directed at the side of the article from sufficient distance that it can scan the entire height of the article in contiguous narrow sections at incident angles close to perpendicular.

One type of device known in the art uses a laser beam emitter unit in which a laser beam is directed at a mirror rotating about a horizontal axis to produce a scanning beam and the scanning beam is deflected by a battery of stationary mirrors onto the article at approximately perpendicular angles of incident. Advantageously, the article has axial symmetry. While the article is being scanned by the beam, it is rotated about its own axis for at least one full rotation so that it may be examined completely. This type of machine is described in French Pat. No. A-2 235 365 and U.S. Pat. Nos. 3,942,001 and 3,987,301.

The rotating mirror usually comprises a wheel having a plurality of mirrored facets. For example, the wheel can be about 15 cm in diameter and have 36 facets, each of which will deflect the beam over an angle of about 20°, in the vertical plane.

Preferably, the article is transported through the process via a star wheel which is a wheel with a plurality of recesses or U-shaped mountings about its circumference for holding the article to be scanned. At the checking station where the article is inspected, a pair of rollers are used to rotate the article. To provide a clear path for the scanning beam, it is highly useful to place the emitter unit at the center of the star wheel.

To be able to check large volume articles over their entire height, for example article about 40 cm tall, the rotating mirror should be placed at an optical distance of over one meter from the article to be checked. At the same time, the battery of stationary mirrors must be relatively close to the light source so that the dimensions of the apparatus are not prohibitive.

A further problem with the apparatus is in the inertial forces produced in high speed operation. To reduce the need to contend with inertial forces it is preferred that the scan be performed on the fly without stopping the rotation of the star wheel. In order to hold the article against the star wheel during the continuous motion a device such as a belt could be placed in frictional contact with the radially outermost portion of the article to be scanned. This device however has not been used in prior art scanners because it produces a blind spot in the scanning of the article by blocking the path of the scanning beam in a portion of the field.

SUMMARY OF THE INVENTION

To alleviate these problems, I have devised a method and an apparatus for scanning transparent or translucent articles. Illustrative apparatus comprises a star wheel adapted for continuous movement of an article to be scanned, a belt for holding the article against the star wheel and providing rotation of the article, and a light box which contains: distributing mirrors that divide a scanning light beam into at least two scanning fields which preferably overlap on the object and a tracking mirror which operates to move the fields with the article.

To scan the article completely without stopping its translational movement, the scanning beam must move with the article. The tracking mirror deflects the path of the scanning beam so it moves with the article through an angle sufficient to scan the entire container. To provide for a more compact apparatus than previously known in the art, a rapid return oscillating mirror is used as the tracking mirror in place of a revolving mirror. The oscillating mirror is preferably placed at a position in the center of the star wheel; and its oscillation is synchronized with the motion of the star wheel.

The light box increases the path of the scanning beam to about four times the usable scanning height (H). The distributing mirrors which produce the plurality of scanning fields are staggered obliquely in the path of the beam. The mirrors are placed at distances along the path ranging from about one quarter the total path length to one half the total path length. Within the light box, an intermediate series of vertical mirrors is placed in the path of the light beam between the oscillating mirror and the distributing mirrors. The intermediate mirrors bend the path around the inside of the light box to produce a path of about twice the scanning height (H) in a compact area. In this way a light box with horizontal dimensions only one eighth the total path length and a height only slightly larger than the field height may be used. The oscillating mirror may be placed a distance from the article to be scanned that is the usable height (H) of the field so that the star wheel has a diameter only twice the usable height of the field.

Following the teaching of the present invention, a machine of less than one meter in diameter can be used with a light field path length of about 1.4 meters. By making only simple adjustments, this machine can be used to scan containers ranging in size from 250 ml to 1250 ml.

As a feature of the invention, about 2° of the scanning field can be used to create an axial scanning field for scanning the bottom of the article. The axial scanning field is diverted to the base by a complementary mirror normally associated with a condenser to bring this light along a caustic located at the opening of the article being examined. This deviating mirror is preferably a curved stationary mirror with a radius of curvature equal to the distance from it to the tracking mirror. The deviating mirror should be adjustably positioned along the path to the tracking mirror.

A small portion of the scanning field is used to excite a photoelectric cell periodically which thus provides clock pulses suitable for synchronizing scans. This makes it possible to locate precisely the point in a scanning cycle where a detected defect is located.

BRIEF DESCRIPTION OF THE DRAWINGS

The preferred embodiment will be described below with reference to the drawings in which:

FIG. 6 is an enlarged view of the oscillating mirror control, taken along line VI—VI of FIG. 2.

DESCRIPTION OF THE PREFERRED EMBODIMENT

Figure 1:
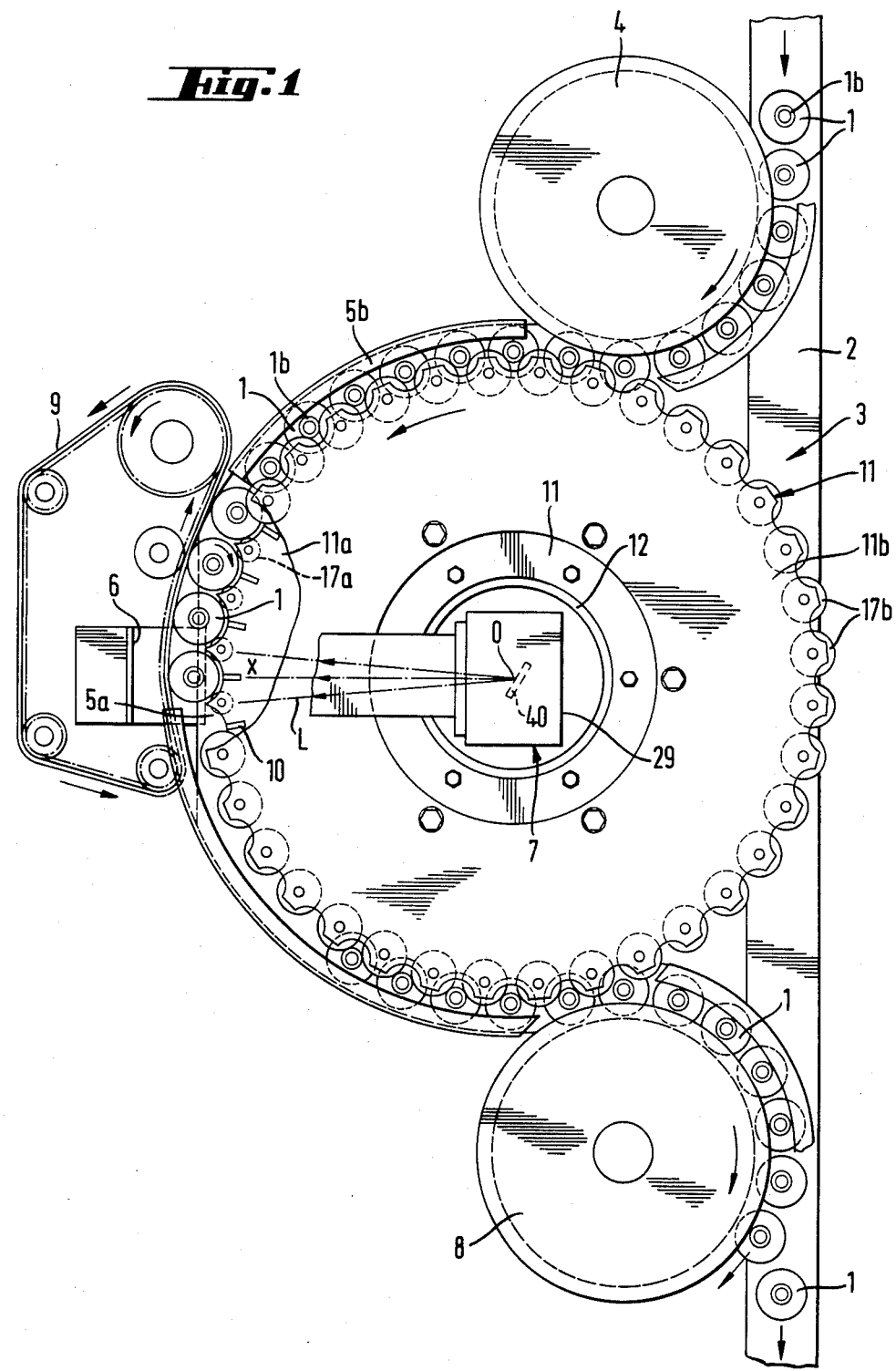
FIG. 1 is a top view of the apparatus with the upper star wheel piece partially cut away.
Figure 2:
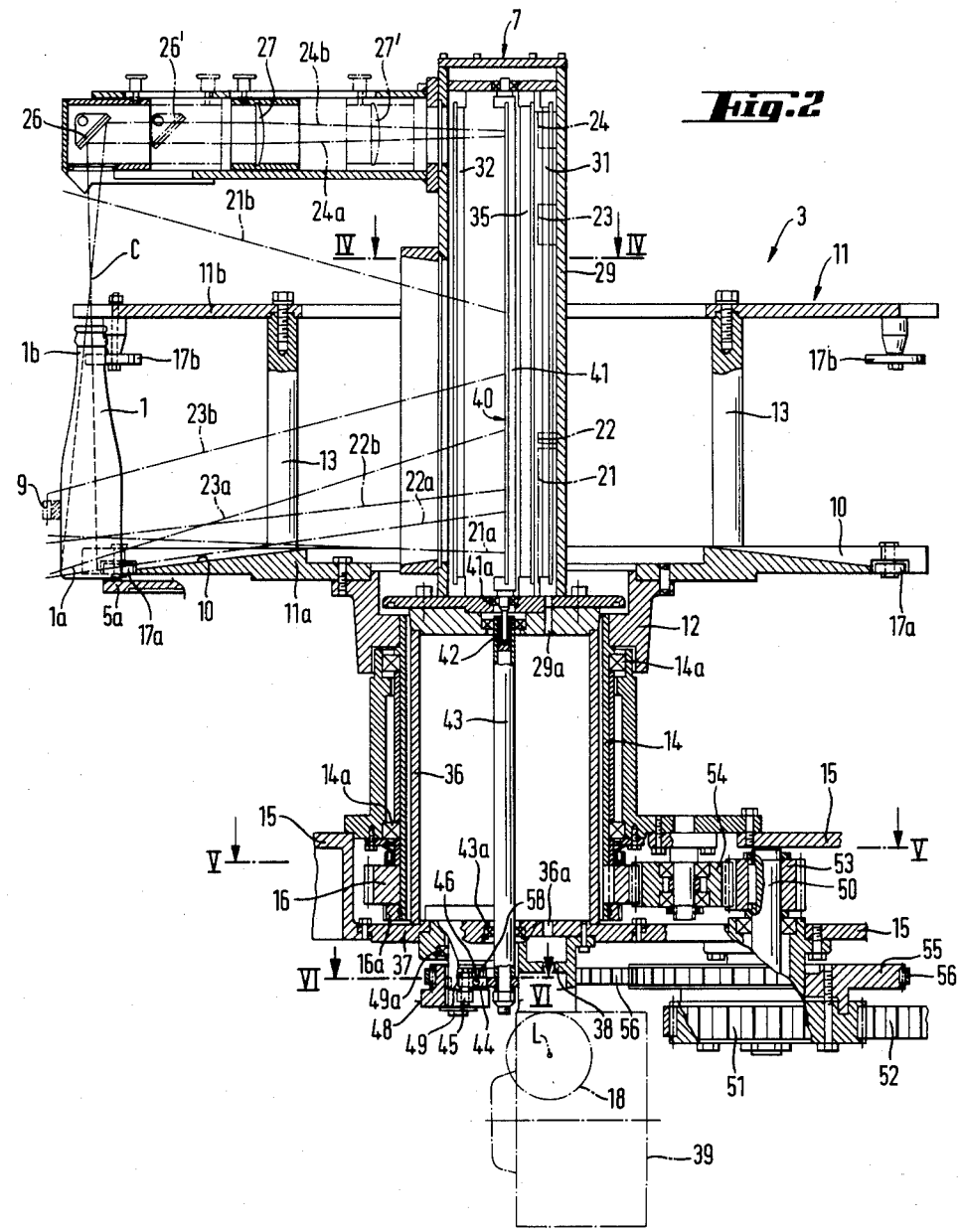
FIG. 2 is a partially cross-sectional side view of the apparatus.

The overall structure of the machine is shown by FIGS. 1 and 2. As shown therein, bottles 1 are transported by a conveyor 2 to a distributing wheel 4 which introduces the bottles to a star wheel 3. On leaving conveyor 2, each bottle 1 rests on portions of a plate 5a and is held within a U-shaped mounting on the star wheel 4 by an outside guide 5b. While on the star wheel, the bottle moves along an arcuate path through several successive stations at which it may be subjected to a series of checks. Of particular interest to the present invention is an optical check performed on the bottle in front of photosensitive screen 6 using a light beam L produced by an emitter element 7. Photosensitive screen 6 illustratively is of the type disclosed in U.S. Pat. No. 3,987,301 the teaching of which is incorporated herein by reference.

The checks are performed without stopping the bottles. The bottles are rotated, while undergoing the check, by a simple or multiple belt 9 moving in the direction opposite to the wheel 3 at the point where their perimeters are contiguous as indicated by the arrows in FIG. 1.

The star wheel preferably comprises a barrel 11 made up of a lower plate 11a, carried by hub 12, and a crown 11b which is held in position with respect to plate 11a by columns 13. In the preferred embodiment, barrel 14 of hub 12 is carried by a double bearing 14a resting on frame 15 of the machine. The barrel and its toothed driving crown 16 are locked in place by screw-in screening ring 16a.

Each bottle 1 rests on portions of plate 5a, while it is located between parts of successive U-Shape mountings. In the checking position, as shown, only a portion of bottom 1a of each bottle contacts the plate. Each bottle is urged against the U-shaped mounting by guide 5b or belt 9. To facilitate rotation, the bottles preferably are urged against lower and upper rollers 17a, 17b in the sides of the U-shaped mountings. As shown in the cut away portion of FIG. 1, bottles in successive U-shaped mountings bear on the same roller located between the successive mountings.

The number of U-shaped mountings, the shape and diameter of the star wheel, and the relative positions of the screen and belt are determined by the size range of bottles to be checked. At a rate of 20 RPM a 36-position star wheel thus makes it possible to inspect 12 articles each second and more than 40,000 articles per hour.

Although the bottles are in motion, their locations are fixed relative to the star wheel. The scan is performed in the vertical plane O-X, which is also fixed relative the star wheel. To check the entire container height, slots or vertical clearances 10 are provided in lower plate 11a of the star wheel to allow a free path for the scanning field light beam.

Figure 3:
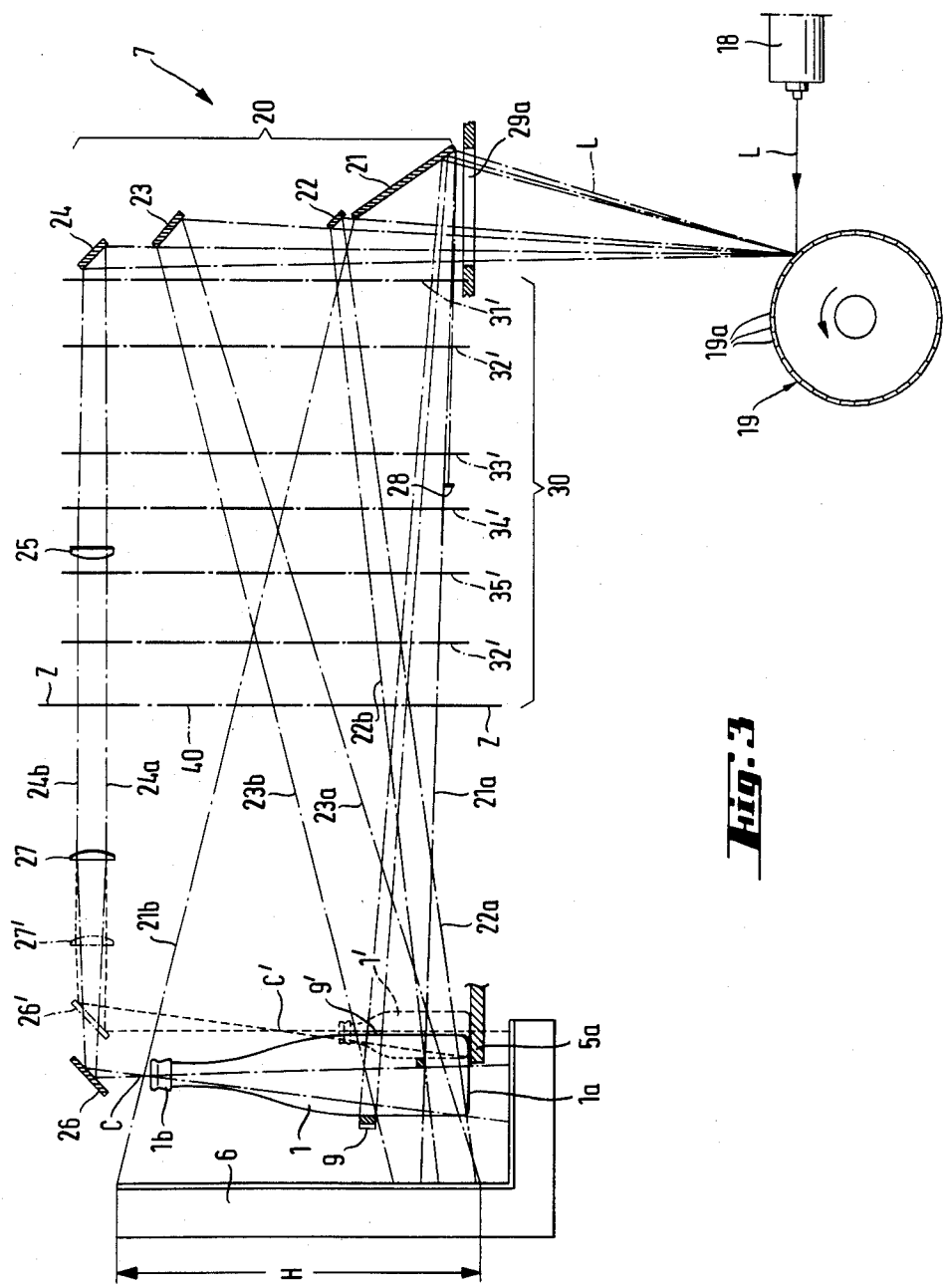
FIG. 3 is a schematic illustration of apparatus used to scan a light beam.

FIG. 3 is a schematic illustration depicting the development of a scanning light beam in the vertical plane.

At the lower portion of emitter 7, a narrow light beam L, generated by a laser 18 is successively reflected by mirrored facets 19a of rotating wheel 19. To produce a beam that scans vertically, the axis of the wheel is horizontal and is perpendicular to the direction of beam L.

Wheel 19 comprises 36 facets 19a from which it is possible to obtain a usable scanning angle or field of about 18° which is only slightly less than the maximum theoretical angle achievable. The wheel 19 rotates at a speed of 6000 RPM. Accordingly, the light beam is scanned at a rate of 3600 times per second.

The beam is reflected by the wheel through aperture 29a towards a battery 20 of four planar mirrors. The mirrors are perpendicular to the plane in which the light beam is scanned and are staggered one behind another at a distance ranging from 40 cm to 80 cm. Thus positioned the mirrors intercept the light over the scanning angle and divide it into 3 main fields and a secondary field. The scanning beam is then directed by a series of mirrors 30 through a folded optical path (FIG. 4) and ultimately through bottle 1 to photosensitive screen 6.

Mirror 21 intercepts approximately a 12° portion of the scanning angle. It is positioned at an angle of about 35° to vertical and directs its portion of the scanning field on an average inclination of about 7° to horizontal. Its portion 21a, 21b of the scanning field passes through the bottle wall twice and checks almost the entire surface of the bottle, despite its considerable height, with the exception of the bottle's lower portion and the portion 9' blocked by belt 9.

Mirror 22 intercepts a smaller portion of the scanning angle, approximately 1° and is inclined at about 45°. Mirror 22 directs its portion 22a, 22b of the scanning field to the bottom of the article being checked at an average inclination of −7° to horizontal. This makes it possible to reach the lower part of the bottle. The scanning by mirrors 21, 22 thus covers the entire useful height H except for a "blind angle" at portion 9'.

Mirror 23 is placed even higher above the star wheel 3 and is inclined at about 50° to vertical to intercept a portion of approximately 3° of the scanning angle. Mirror 23 directs its portion 23a, 23b of the scanning field at an average inclination of −16° to the upper portion of the lower third of height H. This makes it possible to inspect this part of the bottle at a sufficient inclination to check the zone 9' which escaped the portion of the field created by mirror 21.

Mirror 24 creates a secondary beam 24a, 24b which is picked up by a narrow cylindrical lens 25 to create a parallel scanning beam. This beam is focused by cylindrical lens 27 and directed downward by reflection 26 so as to come to focus at an angle of approximately 7° at point C near neck 1b of the bottle. As a result, the beam passes through the open neck of the bottle and illuminates bottom 1a, outside of plate 5a, over an entire radius.

Thus, during a complete revolution of the bottle in front of screen 6, the scanning beam illuminates each portion of the bottle wall at least once.

Advantageously, at the beginning of each vertical scan, a small portion of the field portion created by mirror 21 is picked up by photoelectric diode 28 (FIG. 3) in order to mark the beginning of each pass of the scanning beam.

To use the machine for bottles of different dimensions such as bottle 1' of FIG. 3, only a few minor adjustments need be made. Thus the mirror 26 is moved to 26' to bring it above the neck of bottle 1'; and lens 27 is moved to 27' to lower the point of convergence of the light rays to C' near the neck of bottle 1'. Finally belt 9 is adjusted to compensate for the difference in height of bottle 1'.

Figure 4:
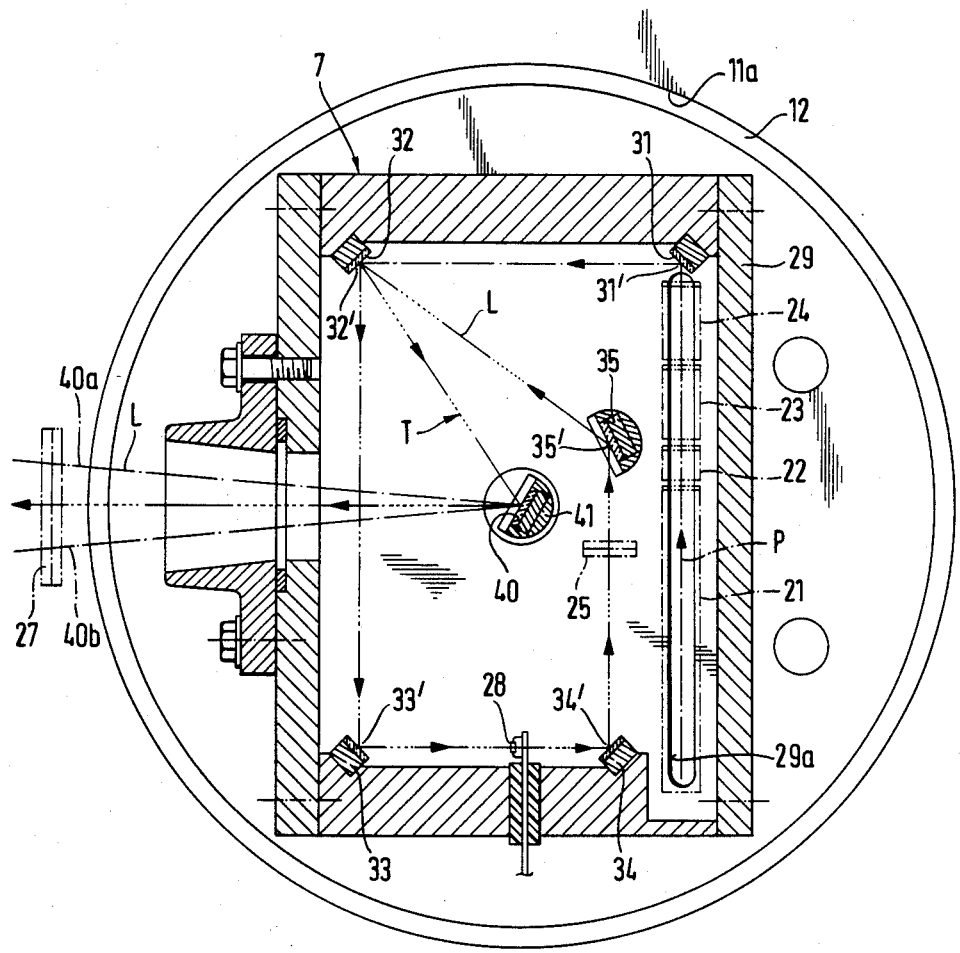
FIG. 4 is a view of a light box taken along line IV—IV of FIG. 2.

As shown in FIG. 4, the four mirrors 21–24 of battery 20 are mounted within the light box 29 of the emitter 7 directly over slit aperture 29a. As will be apparent the actual orientation of slit aperture 29a and mirrors 21–24 in FIG. 4 is at right angles to the orientation shown in FIG. 3 for purposes of illustrating the scanning of the laser beam.

Included within the light box 29 is a series of mirrors 30 to fold the path of the scanning beam in order to provide for an optical path which is longer than if the beam traveled on a straight line from the mirror battery 20 to the article to be scanned. Mirrors 30 comprise vertical mirrors 31–35 which bend the vertical plane of the scanning beam without distorting it. As a result, the scanning beam travels a path T that is bent about successive vertical axes 31'–35' indicated in both FIGS. 3 and 4.

Mirrors 31–33 are placed in the path of the scanning beam in three successive corners of light box 29. Each mirror is set at a 45° angle to the plane of the light beam and folds the path of the beam so that it travels around the inside of the box. Mirror 34 is placed to deflect the path to mirror 35 which, in turn, directs the path toward mirror 32. Mirror 32 reflects the path to oscillating mirror 40 which is placed in the center of the box on axis Z shown in FIG. 3 which axis coincides with the axis of the star wheel 3.

As shown in FIG. 2, light box 29 is mounted on case 36 which goes into the hub of the star wheel and rests on a cover of frame 15 of the machine. A column 38, which is also supported by frame 15, is used to fasten a case 39 of rotating wheel 19. An aperture 36a is provided by case 36 to provide a clear path for the scanning beam produced by wheel 19 and laser 18.

Mirror 40 is adapted for oscillation about axis Z and thus moves the scanning field horizontally between 40a and 40b (FIG. 4) which corresponds to the angular motion of a bottle in the star wheel during a checking operation. As will be appreciated by those skilled in the art, the mirror oscillates with an angular amplitude one half the angle between 40a and 40b. The angle between 40a and 40b is slightly less than the angle between two radii running from the axes of two successive articles to the axis of the star wheel. The minimum width of screen 6 corresponds to the travel of the beam from 40a to 40b.

Cylindrical lens 25 is placed between mirrors 34 and 35, only in the path of the scanning beam deflected by mirror 24. Lens 25 redirects the portion 24a, 24b of the beam incident on it so that this portion, which diverges from the facets of wheel 19, is made substantially parallel. Cylindrical lens 27 which follows mirror 40 is likewise located only in the path of the beam deflected by mirror 24. It acts like a prism with horizontal parallel faces to converge the light rays in that portion of the beam at point C.

Mirror 26 is used to deviate the path of the field created by mirror 24 down into the neck of the bottle. If this mirror were planar, the distance from axis Z to the mirror would vary over a scanning oscillation period which would produce undesirable results. It is possible to eliminate this problem by using a series of small mirrors mounted on the star wheel above each bottle and which travel with each bottle. However, it is simpler and therefor preferred to use a single stationary mirror which is curved so that the focal point C follows the path of the neck of the bottle more closely. Advantageously, the surface of the mirror coincides with a surface defined by revolution about axis Z; but this is not required. It is possible to use a mirror that is conical, cylindrical or spherical with a curvature that is appropriate for use at a distance half-way between the extreme positions of use, 26 and 26' of FIG. 3.

Various systems may be used to provide mirror 40 with its oscillating motion. However, a camming system is used in the preferred embodiment because it provides regularity of movement and flexibility in use. The control system appears in FIG. 2 and its transmission is shown in more detail in FIGS. 5 and 6.

Figure 5:
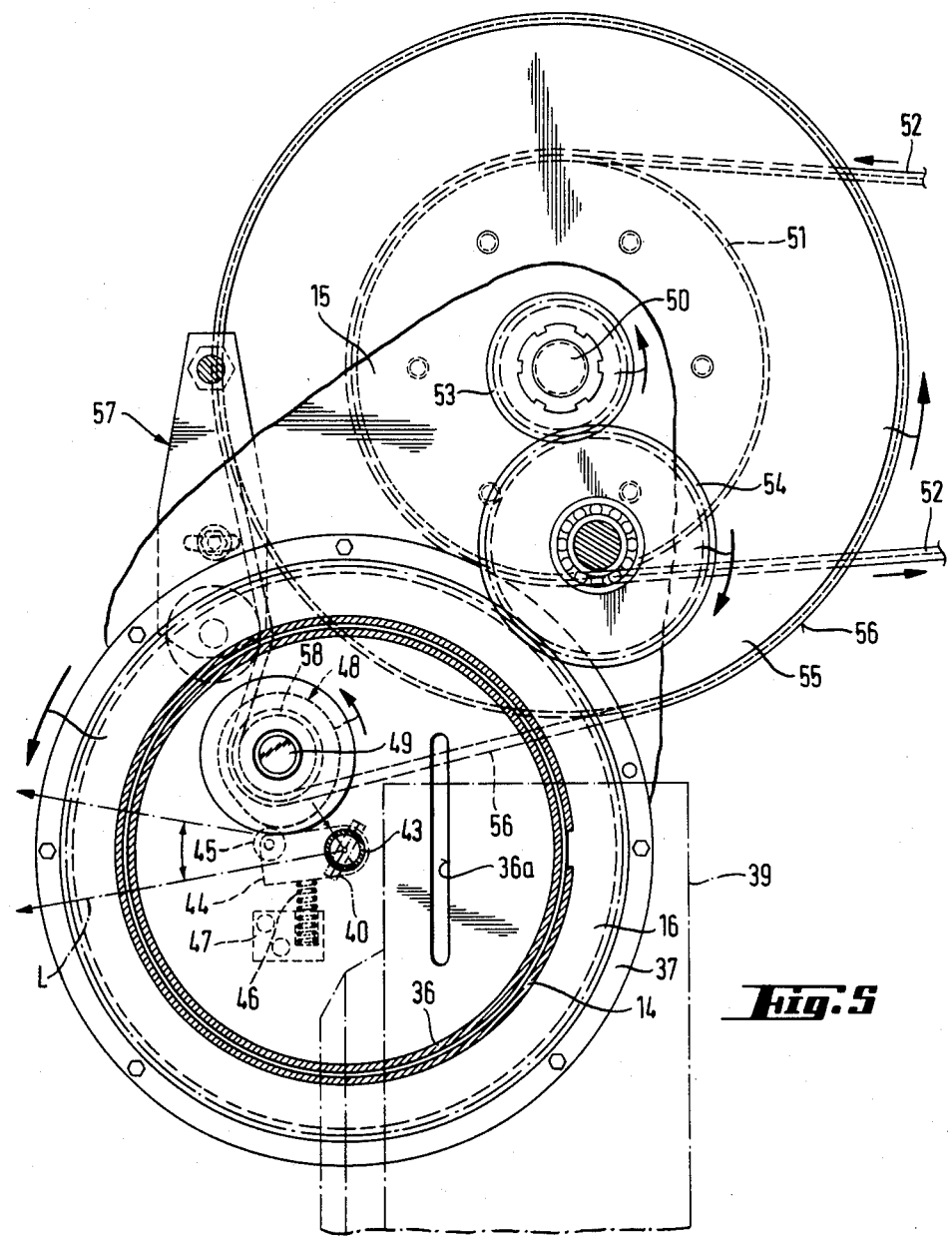
FIG. 5 is a top view of the transmission taken along line V—V of FIG. 2.

Oscillating mirror 40 is carried by a shaft 41 mounted between two bearings 41a. Shaft 41 is engaged, by a flexible coupling, with a transmission shaft 43 which is mounted between two bearings 43a in case 36. An arm 44 shown in FIGS. 3, 5 and 6 is coupled to shaft 43. Arm 44 is provided with a roller 45 and is biased into contact with cam 48 by spring 46 which butts against stop 47. Cam 48 is mounted at the end of drive shaft 49 which turns in a double bearing 49a.

Cam 48 has a uniformly rising portion which moves arm 44 through roller 45 and thereby makes mirror 40 turn in the same direction as star wheel 3 but at a rotational speed of half the rotational speed of the star wheel. At about point 48b the cam allows a rapid but braked return of the mirror to its initial position. The cam therefor makes one revolution per cycle and is in phase with the star wheel such that it makes one revolution each time the star wheel advances an amount equal to the angular separation of two radii between the star wheel axis and two successive U-shaped mountings. The controlled travel of the mirror therefor creates the available angle of observation.

In order to maintain synchronization, cam 48 and star wheel 3 are driven from the same distributor shaft 50 (FIG. 5). This shaft carries a driven pulley 51 connected to the motor of the machine (not shown) by a transmission belt 52. The transmission belt 52 may also drive accessories such as belt 9 (FIG. 1). The shaft 50 engages the ring gear 16 of the star wheel by gear train 53 and 54 in a ratio of 4:1. The shaft 50 also carries a toothed pulley 55 which is connected via notched belt 56 to a driven toothed pulley 58 mounted on drive shaft 49. The notched belt is kept under the proper tension by tightener 57.

Cam 48 and pulley 58 are an integral unit which is keyed onto shaft 49. The unit can be of three different forms which depend on the type of star wheel. The groove diameters of the wheels of the three different forms change in proportion to the angles 10°, 12° and 15° separating the U-shaped mountings on three different star wheels so as to provide step down ratios of 9:1, 7.5:1 and 6:1 respectively. As a result, the step down ratio between the wheel and cam take values of 36, 30 and 24, respectively, which correspond to the number of U-shaped mountings on the circumference of the star wheel. The corresponding cams have the same average diameter but their radius variation is proportional to the tracking angle after taking into account the idle return time of the mirror to its initial position prior to each tracking. Each cam moves the arm 44 through roller 45 once per cycle imparting to the oscillating mirror 40 a tracking movement of angular rotational amplitude equal to one half the tracking angle.

Although this description has been of a limited number of embodiments of the invention it is understood that variations can be made by those skilled in the art while still coming under the spirit and scope of this invention.

What is claimed is:

1. An apparatus for optical checking of transparent or translucent objects comprising a star wheel for transporting said objects in continuous movement, means in peripheral contact with an object to rotate such object while it is being transported by said star wheel, means for generating a laser light beam, said laser light beam being directed onto a revolving mirror which directs the beam to a plurality of distributing mirrors in a multiple reflection light box to create an oscillating laser light beam field, means for tracking said object to be checked with said oscillating light beam field while said object is rotated, and photosensitive receiver means for receiving said laser light beam
characterized in that:
   (a) the means which rotate said object contact said object at an intermediate height on said object; and
   (b) said distributing mirrors make at least two distinct portions of said laser light beam field converge on said object at differing average angles of inclination such that the entire surface of the object can be checked by avoiding any blind spot created by said means which rotate said object.

2. The apparatus according to claim 1 wherein said means provided for having said laser light beam field track said object comprises a rapid return oscillating mirror synchronized with the advance of the star wheel.

3. The apparatus according to claim 2 wherein said oscillating mirror oscillates about an axis which is coaxial with that of said star wheel.

4. The apparatus according to claim 2 wherein said oscillating mirror is oscillated by means of a cam controlling the rotation of shaft means attached to said oscillating mirror.

5. The apparatus according to claim 4 wherein said cam makes one rotation per oscillation cycle and comprises a uniformly rising portion to provide motion to the oscillating mirror such that said oscillating mirror rotates at one half the rotational speed of the star wheel.

6. The apparatus according to claim 5 wherein said cam and star wheel are driven by the same distributor shaft, the cam being coupled to said distributor shaft via notched belt means and toothed pulleys.

7. The apparatus according to claim 6 wherein said cam and its associated toothed pulley are an integral unit such that a first unit may be interchanged with a second unit of dimensions differing from the first unit to change the period or amplitude of oscillation of said oscillating mirror.

8. The apparatus of claim 1 wherein the object is rotated for at least one full rotation while the laser light beam scans it in successive diametric planes.

9. The apparatus according to claim 1 wherein a portion of said laser light beam field is directed to illuminate the bottom of said object after deviation by a complementary mirror bringing the illumination along a caustic located at the opening of said object.

10. The apparatus according to claim 9 wherein said complementary mirror is a curved stationary mirror.

11. The apparatus according to claim 10 wherein the radius of curvature of said complementary mirror is substantially the same as the distance from the star wheel axis to the location of the complementary mirror.

12. The apparatus of claim 11 wherein the complementary mirror is associated with adjustable condenser means comprising a cylindrical lens.

13. The apparatus according to claim 1 wherein said light box comprises a series of reflector means for folding the path of said laser light beam to increase the optical distance it travels before reaching the object beyond the physical distance between the laser beam generating means and said object.

14. The apparatus according to claim 13 wherein the distance between said oscillating mirror and said object to be scanned is substantially the same as the useful height of the scanning field as it passes through the object to be scanned.

15. The apparatus according to claim 13 wherein said series of reflector means comprises a series of vertical planar mirrors which route the path of the laser light beam about the inside of the light box and finally direct said laser light beam onto the tracking means.

16. The apparatus according to claim 1 wherein the object to be scanned is urged into a U-shaped mounting on the star wheel periphery, which comprises double roller trains common to successive U-shaped mountings, by a belt which also provides said objects to be scanned with their rotational motion.

17. An apparatus for optical checking of transparent or translucent objects comprising means for transporting said objects in continuous movement along an arcuate path, means in peripheral contact with an object to rotate said object, means for generating a laser light beam for optically checking said object, said laser light beam being directed onto a revolving mirror which reflects the beam onto a plurality of distributing mirrors which create an oscillating laser light beam field having at least two distinct portions, said mirrors being oriented so that two distinct portions of the laser light beam field converge on said object at differing average angles of inclination such that blind spots created by apparatus members that block the path of at least one portion of said laser light beam field are scanned by at least another one of said portions, means for tracking said object to be checked with said laser light beam field, and a photosensitive receiver for receiving said laser light beam field after it passes through said object.

18. An apparatus for optical checking of transparent or translucent objects comprising a star wheel for transporting said objects in continuous movement, means in peripheral contact with an object to rotate such object while it is being transported by said star wheel, means for generating a laser light beam, said laser light beam being directed onto a scanning mirror which directs the beam to a plurality of distributing mirrors in a multiple reflection light box to create an oscillating light beam field, means for tracking said object to be checked with said oscillating light beam field while said object is rotated, and photosensitive receiver means for receiving said laser light beam field, wherein the light box has within it a plurality of reflecting means which reflect the laser light beam field about a folded path such that the distance along the optical path of the laser beam from the laser generating means to the object is greater than the physical distance between them.

19. A method of optically checking transparent or translucent objects comprising:
 (a) generating a laser light beam;
 (b) creating an oscillating laser light beam scanning field by directing said laser beam to at least one scanning mirror;
 (c) dividing said laser light beam scanning field into at least two distinct portions;
 (d) directing said portions onto at least one of said objects at differing average angles of inclination such that they scan the entire surface of said object with at least one of said portions scanning blind spots in the field of another of said portions; and
 (e) receiving said laser light beam scanning field at a photosensitive receiver means after it passes through said object.

20. A method of optically checking transparent or translucent objects comprising:
 (a) generating a laser light beam;
 (b) directing said laser light beam onto a revolving mirror to create an oscillating laser light beam field;
 (c) reflecting said laser light beam field along a folded path to increase the length of the optical path said laser beam follows above the physical distance between its source and said object in order to produce average angles of inclination of said laser light beam field substantially perpendicular to said object's surface while scanning the entire height of said object; and
 (d) receiving said oscillating laser light beam field on photosensitive receiving means after said oscillating laser light beam field passes through said object.

* * * * *